(12) United States Patent
Vann

(10) Patent No.: US 7,014,470 B2
(45) Date of Patent: Mar. 21, 2006

(54) RISK REDUCTION TEACHING MODULES

(75) Inventor: Rob Vann, Overland Park, KS (US)

(73) Assignee: High Plains Marketing, Overland Park, KS (US)

( * ) Notice: Subject to any disclaimer, the term of this patent is extended or adjusted under 35 U.S.C. 154(b) by 0 days.

(21) Appl. No.: 10/417,728

(22) Filed: Apr. 16, 2003

(65) Prior Publication Data

US 2004/0014015 A1 Jan. 22, 2004

Related U.S. Application Data

(60) Provisional application No. 60/373,045, filed on Apr. 16, 2002.

(51) Int. Cl.
*G09B 23/28* (2006.01)
(52) U.S. Cl. .............................. 434/262; 705/2; 705/3
(58) Field of Classification Search ................ 434/262; 705/2, 3
See application file for complete search history.

(56) References Cited

U.S. PATENT DOCUMENTS

| | | | | |
|---|---|---|---|---|
| 5,791,907 A | * | 8/1998 | Ramshaw et al. | 434/262 |
| 5,791,908 A | * | 8/1998 | Gillio | 434/262 |
| 5,867,821 A | * | 2/1999 | Ballantyne et al. | 705/2 |
| 6,171,112 B1 | * | 1/2001 | Clark et al. | 434/322 |
| 6,535,714 B1 | * | 3/2003 | Melker et al. | 434/350 |
| 6,551,107 B1 | * | 4/2003 | Buckley et al. | 434/262 |
| 2001/0032099 A1 | * | 10/2001 | Joao | 705/2 |
| 2002/0178031 A1 | * | 11/2002 | Sorensen et al. | 705/2 |
| 2002/0194025 A1 | * | 12/2002 | Notelovitz | 705/2 |

* cited by examiner

*Primary Examiner*—Chanda L. Harris
(74) *Attorney, Agent, or Firm*—Hovey Williams LLP

(57) ABSTRACT

A teaching module (10) and method for enhancing skills and reducing risks in the practice of medicine or other areas of healthcare. Each module (10) comprises a multi-media presentation of information relating to a variety of important aspects of a particular healthcare-related topic, such as, for example, a medical technique or technology, including enhancing skills and reducing risks associated with that technique or technology. Skill enhancement information is reviewed by relevant healthcare practitioners, and risk reduction information is reviewed by a malpractice attorney. Each module (10) is added to a virtual web-based library of similar modules so as to be accessible anywhere and at anytime. Review may be sought to approve the module (10) for use in satisfying continuing medical education credit requirements, malpractice insurance premium reduction, or license renewal. A test may be developed and administered for testing user understanding or retention of the information.

21 Claims, 2 Drawing Sheets

RISK REDUCTION TEACHING MODULES

RELATED APPLICATIONS

The present application claims priority benefit, with regard to all common subject matter, of an earlier-filed U.S. provisional patent application titled SKILL ENHANCEMENT MODULES, Ser. No. 60/373,045, filed Apr. 16, 2002. The identified earlier-filed application is hereby incorporated by reference into the present application.

BACKGROUND OF THE INVENTION

1. Field of the Invention

The present invention relates broadly to multi-media teaching and reference tools. More particularly, the present invention concerns a teaching module and virtual library of such modules and an associated method, wherein each module comprises a multi-media presentation of information relating to a variety of important aspects of a particular medical or other healthcare technique or technology, including enhancing skills and reducing risks associated with that technique or technology.

2. Description of the Prior Art

Physicians and other healthcare practitioners are frequently subjected to expensive medical malpractice claims and lawsuits. Damage awards and other costs associated with such suits profoundly impact the practice of medicine and healthcare generally. As a result, some medical malpractice insurance carriers are refusing to provide coverage; some physicians are closing their practices or facing bankruptcy; and some new or replacement insurance policies are costing four and even five times more than existing policies. Though high-risk fields, procedures, and practitioners can be identified, there are few options available for effectively reducing risks of patient injury or dissatisfaction and risks of malpractice. There are, for example, approximately 25,000 surgeons in the United States, of which those with less than two years of experience or greater than fifteen years of post-residency or post-fellowship experience are considered to have the highest risks of malpractice.

While it is desirable to provide these practitioners with resources and tools for improving surgical or other treatment techniques, there are other perhaps equally important aspects of a successful practice that are often ignored. Publications, seminars, presentations, classes, and similar resources or tools, including continuing medical education (CME) seminars, are known that each teach or convey one or more but less than all of these pertinent and necessary aspects. For example, resources or tools that focus on technical issues surrounding a procedure or technology often ignore risk and malpractice issues or other legal or ethical issues. One reason for this may be the diversity of perspectives needed to fully appreciate and address all such important aspects of a medical or healthcare practice.

Furthermore, these resources or tools often involve in-person, group attendance at a centralized location, which can give rise to substantial expenses for travel and accommodations as well as significant absences from work. Additionally, these resources or tools, particularly those that require in-person attendance, are rarely immediately available whenever or wherever needed and therefore may impart general knowledge but are of little or no assistance in specific cases.

Due to the above-identified and other problems and disadvantages in the art, a need exists for an improved mechanism for teaching a broad variety of important aspects of medical and healthcare practice.

SUMMARY OF THE INVENTION

The present invention overcomes the above-described and other problems and disadvantages in the prior art with a teaching module and virtual library of such modules and an associated method, wherein each module comprises a multi-media presentation of information relating to a variety of important aspects of a particular healthcare-related topic, such as, for example, a medical technique or technology, including enhancing skills and reducing risks associated with that technique or technology.

Each module broadly includes a skill enhancement information component and risk reduction information component. The information is primarily presented in the form of a PowerPoint presentation by an appropriate person, typically a surgeon or other relevant medical or healthcare practitioner, who is assisted or advised by a medical malpractice attorney. The presentation is enhanced with appropriate multi-media aids, and may also be enhanced with appropriate output of a relevant medical testing or monitoring instrument or device.

Broadly, each module preferably substantially follows a general formula for content, depending on the nature of the particular healthcare-related topic. It will be appreciated by both healthcare practitioners and those in the teaching arts that this formula is unique in that it incorporates and blends for the student, viewer, or other user three elements that, in the prior art, had to be accessed separately, typically at substantial inconvenience and expense. These elements are cognitive, technical, and risk reduction.

Once a preliminary draft of the module is complete, a group of relevant doctors or other healthcare practitioners reviews and, as necessary, edits or assists in editing the skill enhancement component of the presentation. Similarly, one or more medical malpractice attorneys edits or assists in editing the risk reduction component of the presentation to ensure that it is properly and sufficiently risk informative. Thus, the finished module uses a strategic blend of cognitive, technical, and risk reduction tips to provide an effective tool for substantially reducing or eliminating patient injury or dissatisfaction as well as malpractice claims.

Preferably, a plurality of such modules are created covering a broad range or variety of topics. The modules are added to a virtual web-based library that can be accessed from substantially anywhere and at anytime. To facilitate quick and convenient searching and access, modules are preferably cataloged by topic, author, and academic affiliation.

Furthermore, the presentations are preferably adapted or tailored as necessary to achieve accreditation or approval for use in satisfying continuing medical education (CME) credit requirements, malpractice insurance premium reduction, or license renewal.

Additionally, written examinations or other testing mechanisms or forms of testing, including, for example, web-based testing, may be developed and administered to test the user's understanding or retention of the information presented. The test may be mandatory or voluntary. In a preferred implementation, the test is electronic and incorporated into or otherwise automatically or optionally associated with the module so that grading is performed and feedback is provided substantially automatically and immediately. Such testing may be particularly advantageous or desirable for high-risk practitioners or practitioners performing high-risk procedures.

Thus, it will be appreciated that the present invention provides a number of substantial advantages over the prior art, including, for example, providing a virtual web-based library of teaching modules that combine both skill enhancement and risk reduction information in a single presentation that is available substantially anywhere and at any time without requiring of inconvenient or costly travel or missed work. The information presented is designed particularly to improve the practitioner's technical skills and thereby enhance quality of care and reduce risks of adverse events; make the practitioner more aware of patterns of any adverse events; inform the practitioner of common causes of patient dissatisfaction or malpractice claims associated with the technique or technology; and instruct the practitioner on any actions that could or should be taken to reduce the risk of patient injury, dissatisfaction, and malpractice claims. Thus, it is contemplated that use of the modules may decrease malpractice insurance premiums by reducing the incidence of avoidable patient injuries or dissatisfaction and, more, generally, improving the quality of patient care.

These and other important features of the present invention are more fully described in the section titled DETAILED DESCRIPTION OF A PREFERRED EMBODIMENT, below.

BRIEF DESCRIPTION OF THE DRAWINGS

A preferred embodiment of the present invention is described in detail below with reference to the attached drawing figures, wherein.

DETAILED DESCRIPTION OF A PREFERRED EMBODIMENT

With reference to the figures, a teaching module 10 and associated method of enhancing skills and reducing risks in the practice of medicine or other areas of healthcare is described and disclosed constructed in accordance with a preferred embodiment of the present invention. More particularly, the present invention concerns a teaching module 10 and virtual library of such modules, wherein each module 10 comprises a multi-media presentation of information relating to a variety of important aspects of a particular healthcare-related topic, such as, for example, a medical technique or technology, including enhancing skills and reducing risks associated with that technique or technology. A contemplated target audience for the modules broadly includes academic programs, including augmenting resident and post-resident education and training, and high-risk practitioners, particularly surgeons with less than two years of experience or more than fifteen years of post-residency or post-fellowship experience.

Figure 1:
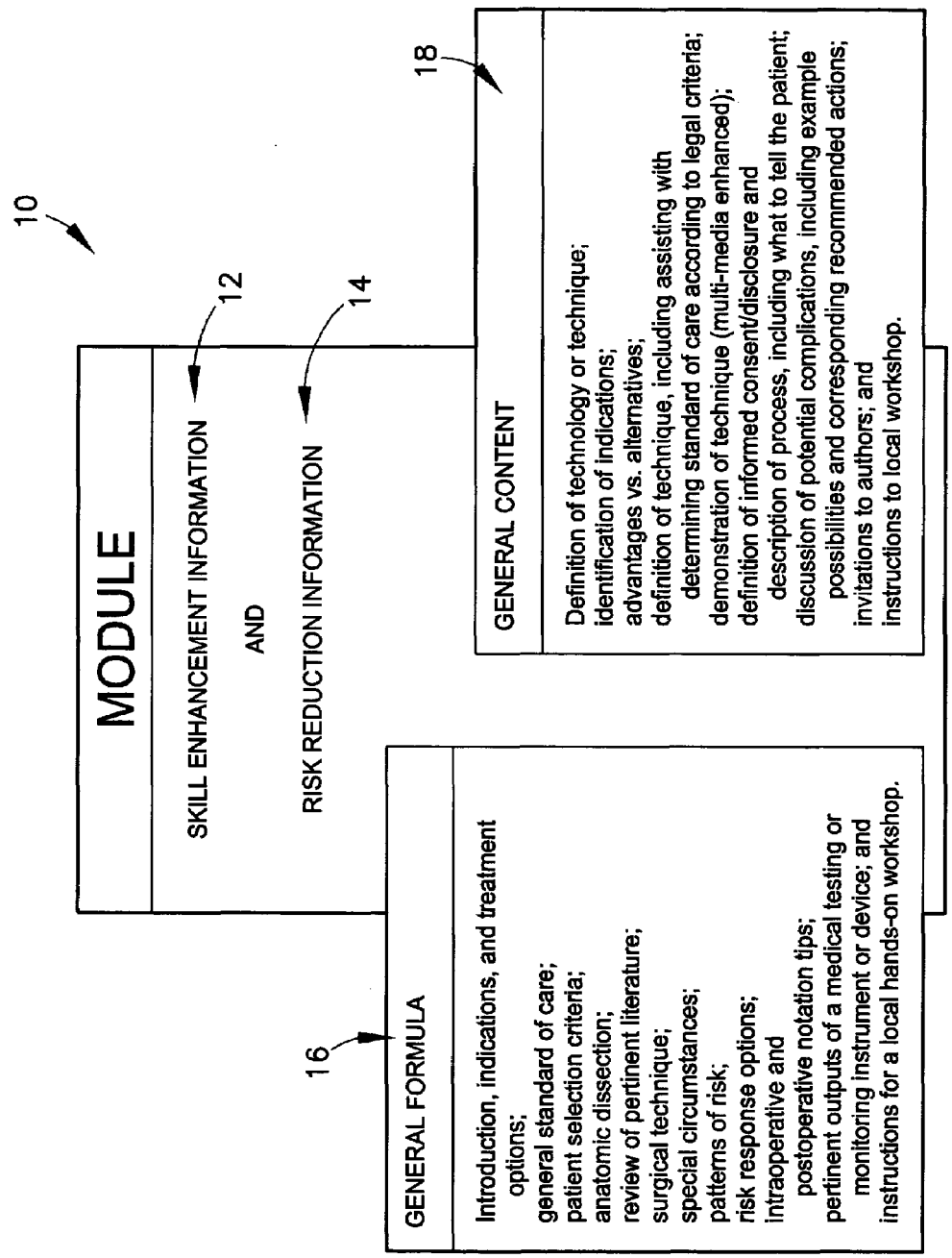
FIG. 1 is a depiction of a preferred embodiment of the module of the present invention.

Referring to FIG. 1, each module 10 broadly includes a skill enhancement information component 12 and risk reduction information component 14. The information is recorded or stored on a suitable storage, recording, or memory medium, such as, for example, a copy-protected compact disk (CD) or server harddrive so as to be accessible, playable, or executable by any conventional desktop or portable computing device having a CD drive or Internet access.

The information is primarily presented in the form of a PowerPoint presentation by an appropriate person, typically a surgeon or other relevant medical or healthcare practitioner, who is assisted or advised by a medical malpractice attorney. The presentation is enhanced with appropriate multi-media aids, such as, for example, audio or video clips; still images or slides; graphics or animated graphics; and text. The presentation may also be enhanced with x-rays, radiographs, or other appropriate output of a relevant medical testing or monitoring instrument or device. The presentation itself is preferably substantially automated to facilitate the viewing process.

Broadly, each module 10 preferably substantially follows the following general formula 16 for content, with allowances being made for the nature of the particular healthcare-related topic:
  introduction, indications, and treatment options;
  general standard of care;
  patient selection criteria;
  anatomic dissection;
  review of pertinent literature;
  surgical technique;
  special circumstances;
  patterns of risk;
  risk response options;
  intraoperative and postoperative notation tips;
  pertinent outputs of a medical testing or monitoring instrument or device (e.g., x-rays, radiographs);
  instructions for a local hands-on workshop, if any.

It will be appreciated by both healthcare practitioners and those in the teaching arts that this formula 16 is unique in that it incorporates and blends for the student or viewer three elements that, in the prior art, had to be accessed separately, typically at great inconvenience. These elements are cognitive, technical, and risk reduction.

Broadly, each module 10 preferably includes the following content 18, with allowances being made for the nature of the particular healthcare-related topic:
  definition of technology or technique;
  identification of indications;
  advantages vs. alternatives;
  definition of technique, including assisting with determining standard of care according to legal criteria;
  demonstration of technique (multi-media enhanced);
  definition of informed consent/disclosure and description of process,
  including what to tell the patient;
  discussion of potential complications, including example possibilities and corresponding recommended actions;
  invitations to authors;
  instructions to local workshop, if any.

The aforementioned local workshop may be an in-person opportunity for hands-on experience that reflects, corresponds to, or build upon the information presented by the module 10. The local workshop is substantially optional; some topics, particularly some techniques or technologies, may draw greater benefit from such a workshop than others. If used, the workshop is preferably truly local, rather than state-wide or regional, so that inconvenient and costly travel or missed work is not required in order to attend.

Once a preliminary draft of the module 10 is complete, a group of relevant doctors or other relevant healthcare practitioners reviews and, as necessary, edits or assists in editing the skill enhancement component 12 of the presentation.

Similarly, one or more medical malpractice attorneys reviews and, as necessary, edits or assists in editing the risk reduction component 14 of the presentation to ensure that it is properly risk informative. Thus, the finished module 10 uses a strategic blend of cognitive, technical, and risk reduction tips to provide an effective tool for substantially reducing or eliminating patient injury or dissatisfaction as well as malpractice claims.

Once the module 10 has passed both medical and legal review, it may be made available for use. Preferably, a plurality of modules, substantially similar or identical to the module 10 described above, are created covering a broad range or variety of topics. As an example, contemplated module topics for the specific area of orthopedic surgery may include: intertrochanteric; distal radius external fixation; tibia; distal femur; tibial plateau; distal humerus; posterior wall acet; symphyseal plating; ankle; femur; and subtrochenteric.

Preferably, finished modules are added to a virtual web-based library of techniqueor technology-specific modules that can be accessed from substantially anywhere and at any time. Any private or academic practitioner is allowed to access, using a password, any module in the virtual library. To facilitate quick and convenient searching and access, modules are preferably cataloged by topic, author, and academic affiliation. Preferably, if remote access is not possible, the aforementioned copy-protected CDs are available for viewing.

Academic programs, of which there are more than 140 in the United States, are each preferably provided with their own dedicated virtual sub-library to house modules authored by the program's own surgeons or other educators or practitioners.

Thus, each module 10 and virtual library of modules allows for and facilitates access at any time and any place to skill enhancement and risk reduction information in a timely manner and without requiring inconvenient and expensive travel or missed work. The information presented is designed particularly to improve the practitioner's technical skills and thereby enhance quality of care and reduce risks of adverse events; make the practitioner more aware of patterns of any adverse events, patient dissatisfaction, or malpractice claims associated with the technique or technology; inform the practitioner of common causes of patient dissatisfaction or malpractice claims associated with the technique or technology; and instruct the practitioner on any actions that could or should be taken to reduce the risk of patient injury, dissatisfaction, and malpractice claims. Thus, it is contemplated that use of the modules may decrease malpractice insurance premiums by reducing the incidence of avoidable patient injuries or dissatisfaction and, more, generally, improving the quality of patient care.

Furthermore, the presentations are preferably adapted or tailored as necessary to achieve accreditation or approval for use in meeting CME credit requirements. Additionally, the modules may be adapted or tailored as necessary to provide risk reduction information sufficient to qualify the user for reductions in malpractice insurance premiums. Additionally, the modules may be adapted or tailored as necessary to provide skill enhancement information sufficient to support renewal of the viewing practitioner's license.

Additionally, where the presentation refers to particular drugs, appliances, instruments or other relevant items, a telephone number or web-based hyperlink or other appropriate contact information may be given to facilitate the user contacting the maker or manufacturer of the item for additional information or to place an order. It will be appreciated that this feature greatly benefits the maker or manufacturer of the item, such that a fee may be charged for inclusion of the contact information. Other advertising techniques may also be used, including advertisement banners or strategic product placement.

Additionally, written examinations or other testing mechanisms or forms of testing, including, for example, web-based testing, may be developed and administered to test the user's understanding or retention of the information presented. The test may be mandatory or voluntary. In a preferred implementation, the test is electronic and incorporated into or otherwise automatically or optionally associated with the module 10 so that grading is performed and feedback is provided substantially automatically and immediately. Such testing may be particularly advantageous or desirable for high-risk practitioners or practitioners performing high-risk procedures.

Figure 2:
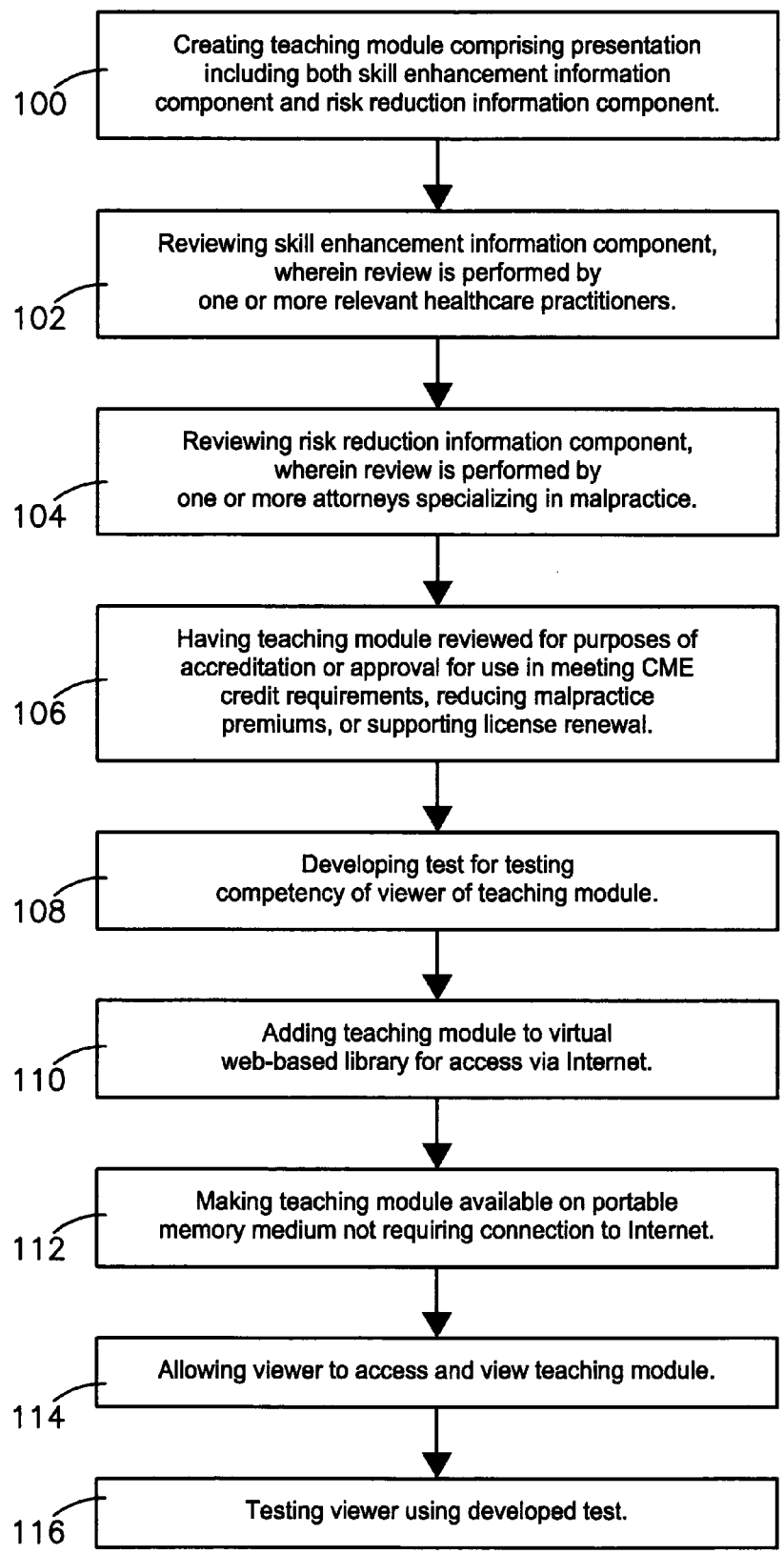
FIG. 2 is a flowchart of steps involved in practicing a preferred embodiment of the method of the present invention.

In exemplary use and operation, the present invention functions as follows. Referring to FIG. 2, a teaching module, substantially similar or identical to the module described above, is created comprising the presentation of both skill enhancement and risk reduction information using the above-described formula and having the above-described content, as depicted in box 100. Following completion of a draft of the module, a group of practitioners reviews and, as necessary, edits the skill enhancement information component of the presentation, as depicted in box 102. Similarly, one or more attorneys familiar with medical malpractice and other relevant legal issues review and, as necessary, edits the risk reduction information component of the presentation, as depicted in box 104.

As desired or required, the module may then be further reviewed by appropriate authorities for purposes of accreditation or approval for use in meeting CME credit requirements, reducing malpractice premiums, or supporting license renewal, as depicted in box 106. Also as desired or required, written examinations or other testing mechanisms or forms of testing are developed and implemented to test and ensure module participation and viewer competency, as depicted in box 108.

The module is then added to or integrated into a virtual web-based library for access via the Internet, as depicted in box 110. The module is also published or otherwise made available on CD or other portable memory medium or storage device to accommodate practitioners who cannot or do not wish to use the Internet, as depicted in box 112.

Thereafter, a resident, perhaps desiring to augment his or her education or training, or a practitioner, perhaps desiring to prepare for a case by learning of or reviewing treatment alternatives, intra-operative tips, risk recognition, and risk response options, accesses, runs, or plays the module and views the substantially automated presentation, as depicted in box 114. Any desired or necessary testing is performed following the presentation, as depicted in box 116.

From the preceding description, it will be appreciated that the teaching module of the present invention provides a number of substantial advantages over the prior art, including, for example, providing a virtual web-based library of teaching modules that combine both skill enhancement and risk reduction information in a single presentation that is available substantially anywhere and at any time without requiring inconvenient or costly travel or missed work. The information presented is designed particularly to improve the practitioner's technical skills and thereby enhance quality of care and reduce risks of an adverse events; make the practitioner more aware of patterns of any adverse events; inform the practitioner of common causes of patient dissatisfaction or malpractice claims associated with the technique or technology; and instruct the practitioner on any actions that could or should be taken to reduce the risk of patient injury, dissatisfaction, and malpractice claims. Thus, it is contemplated that use of the modules may decrease malpractice insurance premiums by reducing the incidence of avoidable patient injuries or dissatisfaction and, more, generally, improving the quality of patient care.

Although the invention has been described with reference to the preferred embodiments illustrated in the accompanying drawings, it is noted that equivalents may be employed and substitutions made herein without departing from the scope of the invention as recited in the claims. For example, the test for testing a user's understanding or retention of the information may be mandatory and administered in-person or it may be voluntary and administered online or as part of the module.

What is claimed is:

1. A method of educating a first healthcare practitioner on skills related to patient treatment and care and a plurality of patterns of risk giving rise to medical malpractice claims, the method comprising the steps of:
    identifying a plurality of skills associated with patient treatment and care for a particular healthcare topic;
    creating a first teaching module incorporating information about the identified skills;
    editing the first teaching module by a second healthcare practitioner to ensure the information incorporated in the first teaching module is correct;
    identifying the plurality of patterns of risk giving rise to the medical malpractice claims and associated with the patient treatment and care;
    creating a second teaching module incorporating the information about the identified risks;
    editing the second teaching module by an attorney; and
    presenting the first and second teaching modules in a multi-media presentation to the first healthcare practitioner so as to enhance the first practitioner's skills and reduce medical malpractice claims.

2. The method as set forth in claim 1, wherein the particular healthcare topic relates to a technique.

3. The method as set forth in claim 1, wherein the particular healthcare topic relates to a technology.

4. The method as set forth in claim 1, wherein the multi-media presentation includes an output of a diagnostic instrument relevant to the particular healthcare topic.

5. The method as set forth in claim 1, wherein the first and second teaching modules are adapted to satisfy a continuing medical education requirement.

6. The method as set forth in claim 5, wherein the first and second teaching modules are adapted to support renewal of a healthcare practitioner's license.

7. The method as set forth in claim 1, wherein the first and second teaching modules are adapted to support a reduction in the first healthcare practitioner's medical malpractice insurance premium.

8. The method as set forth in claim 1, further including a test for measuring understanding of the information of the multi-media presentation.

9. The method as set forth in claim 8, wherein the first and second teaching modules are accessed via a website, and the test is in electronic form and is graded substantially automatically.

10. A method of enhancing skills and reducing risks in healthcare, the method comprising the steps of:
    (a) creating a teaching module comprising a presentation of information concerning a particular healthcare-related topic and including a skill enhancement information component providing information for improving a user's knowledge of a medical procedure and a risk reduction information component providing information for reducing a risk of medical malpractice claims;
    (b) reviewing the skill enhancement information component, wherein review is performed by one or more relevant healthcare practitioners;
    (c) reviewing the risk reduction information component, wherein review is performed by one or more attorneys specializing in malpractice; and
    (d) adding the teaching module to a virtual web-based library for access via an electronic network.

11. The method as set forth in claim 10, further including the step of arranging for the teaching module to be reviewed for purposes of approving use of the teaching module in meeting a continuing medical education credit requirement.

12. The method as set forth in claim 10, further including the step of having the teaching module reviewed for purposes of approving use of the teaching module in reducing malpractice premiums.

13. The method as set forth in claim 10, further including the step of having the teaching module reviewed for purposes of approving use of the teaching module in renewing a license of a healthcare practitioner.

14. The method as set forth in claim 10, further including the step of developing a test for testing understanding following use of the teaching module, wherein the test is incorporated into the teaching module.

15. The method as set forth in claim 14, further including the step of substantially automatically grading and reporting a result of the test.

16. The method as set forth in claim 10, further including the step of allowing a user to search the virtual web-based library for the teaching module based upon a user-specified topic and a user-specified author's name.

17. A method of enhancing skills and reducing risks in healthcare, the method comprising the steps of:
    (a) creating a teaching module comprising a presentation of information concerning a particular healthcare-related topic and including a skill enhancement information component providing information for improving a user's knowledge of a medical procedure and a risk reduction information component providing information for reducing a risk of medical malpractice claims;
    (b) reviewing the skill enhancement information component, wherein review is performed by one or more relevant healthcare practitioners;
    (c) reviewing the risk reduction information component, wherein review is performed by one or more attorneys specializing in malpractice;
    (d) developing a test for testing understanding following use of the teaching module;
    (e) adding the teaching module to a virtual web-based library for access via an electronic network;
    (f) allowing a user to search the virtual web-based library for the teaching module based upon a user-specified topic and a user-specified author's name; and
    (g) testing the user with the test, and substantially automatically grading and reporting a result of the test.

18. The method as set forth in claim 17, further including the step of having the teaching module reviewed for purposes of approving use of the teaching module in meeting a continuing medical education credit requirement.

19. The method as set forth in claim 17, further including the step of having the teaching module reviewed for purposes of approving use of the teaching module in reducing malpractice premiums.

20. The method as set forth in claim 17, further including the step of having the teaching module reviewed for purposes of approving use of the teaching module in renewing a license of a healthcare practitioner.

21. A computer program comprising a combination of code segments stored on a computer-readable medium and executable by a processor, the computer program operable to educate a first healthcare practitioner so as to enhance the practitioner's skills and reduce medical malpractice claims against the practitioner, the computer program comprising:

a code segment operable to provide at least one skill enhancement module to the first healthcare practitioner, the module being edited by a second healthcare practitioner and provided to the first healthcare practitioner for educating the first practitioner on skills related to patient treatment and care; and a code segment operable to provide at least one risk reduction module edited by an attorney for educating the first healthcare practitioner on a plurality of patterns of risk giving rise to medical malpractice claims associated with the patient treatment and care.

* * * * *